(12) United States Patent
Schucker

(10) Patent No.: US 8,344,189 B2
(45) Date of Patent: Jan. 1, 2013

(54) PROCESSES FOR THE RECOVERY OF FUEL-GRADE ETHANOL FROM DILUTE AQUEOUS STREAMS

(75) Inventor: Robert C. Schucker, The Woodlands, TX (US)

(73) Assignee: Trans Ionics Corporation, The Woodlands, TX (US)

( * ) Notice: Subject to any disclaimer, the term of this patent is extended or adjusted under 35 U.S.C. 154(b) by 691 days.

(21) Appl. No.: 12/440,577

(22) PCT Filed: Sep. 7, 2007

(86) PCT No.: PCT/US2007/077832
§ 371 (c)(1), (2), (4) Date: Dec. 10, 2009

(87) PCT Pub. No.: WO2008/031003
PCT Pub. Date: Mar. 13, 2008

(65) Prior Publication Data
US 2010/0108602 A1    May 6, 2010

Related U.S. Application Data

(60) Provisional application No. 60/824,992, filed on Sep. 8, 2006, provisional application No. 60/824,996, filed on Sep. 8, 2006.

(51) Int. Cl.
*C07C 29/74* (2006.01)
(52) U.S. Cl. ...................................... 568/913; 568/918
(58) Field of Classification Search ................. 568/913, 568/918
See application file for complete search history.

(56) References Cited

U.S. PATENT DOCUMENTS 4,692,432 A * 9/1987 Tedder ........................ 568/916
6,861,248 B2 * 3/2005 Dale et al. ................. 435/255.2

* cited by examiner

*Primary Examiner* — Elvis O Price
(74) *Attorney, Agent, or Firm* — Ramey & Browning PLLC

(57) ABSTRACT

A method for recovery of fuel-grade ethanol from dilute aqueous ethanol feed in a continuous or batch-wise process includes providing a feed tank containing a dilute aqueous ethanol liquid phase and a vapor phase, removing a portion of the vapor phase from the tank and circulating it through a membrane contactor having an inner lumen and an outer shell, recovering from the membrane contactor a feed phase substantially reduced in ethanol and a solvent phase substantially enriched in ethanol, separating an enriched ethanol phase from the solvent phase, and removing a substantial amount of water from the enriched ethanol phase to produce a fuel-grade ethanol stream. A Venturi nozzle may be used in lieu of the membrane contactor.

17 Claims, 3 Drawing Sheets

PROCESSES FOR THE RECOVERY OF FUEL-GRADE ETHANOL FROM DILUTE AQUEOUS STREAMS

CROSS-REFERENCE TO RELATED APPLICATIONS

This application claims priority to U.S. Provisional Application No. 60/824,992 filed Sep. 8, 2006 and to U.S. Provisional Application No. 60/824,996 filed Sep. 8, 2006.

BACKGROUND

Under the Clean Air Act of 1990, the Environmental Protection Agency (EPA) was given the authority to set the maximum levels of certain pollutants in the air anywhere in the United States. Since these pollutants arose primarily from automotive exhausts, the concept of reformulated gasoline (RFG) was introduced by the EPA in order to help the cities and states with the highest levels of pollution meet the minimum requirements of the National Ambient Air Quality Standards especially with respect to ozone concentration. Both methyl tertiary butyl ether (MTBE) and ethanol were approved as additives to gasoline for this purpose; and domestic refiners have used MTBE for over a decade.

More recently, however, MTBE has been found to be carcinogenic and, even worse, has been found to be leaking from underground storage tanks into groundwater that serves as a source of drinking water. California was the first state to ban MTBE from gasoline; and, since that time, fifteen other states have instituted MTBE bans.

Congress passed the Energy Policy Act of 2005 creating for the first time a Renewable Fuels Standard (RFS) that committed the United States to the use of ethanol to replace MTBE in gasoline and established a baseline for ethanol usage of 4 billion gallons in 2006. While the Energy Policy Act of 2005 did effectively eliminate the 2% oxygen requirement in RFG set by the Clean Air Act, currently, approximately 30% of the gasoline sold in the United States contains ethanol.

Ethanol is currently produced primarily by fermentation of sugars, starches or cellulose in either a batch or continuous process. The mash is heated to eliminate harmful bacteria prior to fermentation. After transfer to a fermentation tank, yeast is added to promote the production of ethanol, which takes 40-50 hours. During fermentation, the tank is agitated either by a mechanical stirrer or by a gaseous air lift. The product of fermentation is a dilute aqueous ethanol stream commonly called "beer" and containing up to 16-18% ethanol by volume. In order to recover the ethanol from "beer," the liquid (either with or without filtration to remove solids) is fed to a multi-stage distillation column which produces a primary overhead product containing approximately 95 weight percent ethanol. Higher ethanol content cannot economically be achieved by distillation, since ethanol and water form an azeotrope at 96 weight percent ethanol; and the number of distillation trays required to produce this composition would be infinite. As a result, an additional processing step is required involving adsorption by molecular sieve zeolites, which selectively remove water producing a fuel-grade ethanol stream containing greater than about 99 weight percent ethanol.

Both the distillation step to produce 95 weight percent ethanol and the drying of that product using molecular sieves are extremely energy intensive processes resulting in a level of energy required to produce a gallon of ethanol that approaches the energy content of the ethanol produced when burned in gasoline. Therefore, there is a need for an ethanol production process that significantly reduces the energy consumed and results in a much higher "net energy" per gallon of ethanol.

SUMMARY

In one aspect, embodiments disclosed herein relate to a method for recovery of fuel-grade ethanol from dilute aqueous ethanol streams in a continuous or batch-wise process. The method includes the steps of providing a feed tank having a dilute aqueous ethanol feed, which includes a dilute aqueous ethanol liquid phase and a vapor phase, removing a portion of the vapor phase from the tank and circulating it through a membrane contactor having an inner lumen and an outer shell, recovering from the membrane contactor a feed phase substantially reduced in ethanol and a solvent phase substantially enriched in ethanol, separating an enriched ethanol phase from the solvent phase, and removing a substantial amount of water from the enriched ethanol phase to produce a fuel-grade ethanol stream.

In another aspect, embodiments disclosed herein relate to method for the recovery of fuel-grade ethanol from dilute aqueous ethanol streams in a continuous or batch-wise process that includes the steps of providing a feed tank having a dilute aqueous ethanol feed comprising a dilute aqueous ethanol liquid phase and a vapor phase, removing a portion of the vapor phase from the tank by means of a Venturi nozzle having as its working fluid a solvent with an affinity for ethanol, recovering from the Venturi nozzle a feed phase substantially reduced in ethanol and a solvent phase substantially enriched in ethanol, separating an enriched ethanol phase from the solvent phase, removing water from the enriched ethanol phase using a pervaporation membrane to produce a further enriched ethanol stream and an aqueous stream substantially depleted in ethanol, and removing a substantial amount water from the enriched ethanol stream recovered from to produce a fuel-grade ethanol stream.

The foregoing has outlined the features of the present disclosure in order that the detailed description of the invention that follows may be better understood. Additional features and advantages of the invention will be described hereinafter which foam the subject of the claims of the invention.

BRIEF DESCRIPTION OF THE DRAWINGS

The foregoing summary as well as the following detailed description of embodiments disclosed herein will be better understood when read in conjunction with the appended drawings. It should be understood, however, that the present disclosure is not limited to the precise arrangements and instrumentalities shown herein. The components in the drawings are not necessarily to scale, emphasis instead being placed upon clearly illustrating the principles of the present disclosure.

Embodiments disclosed herein may take physical form in certain parts and arrangement of parts. For a more complete understanding of the disclosure, and the advantages thereof, reference is now made to the following descriptions taken in conjunction with the accompanying drawings, in which.

DETAILED DESCRIPTION

Figure 1:
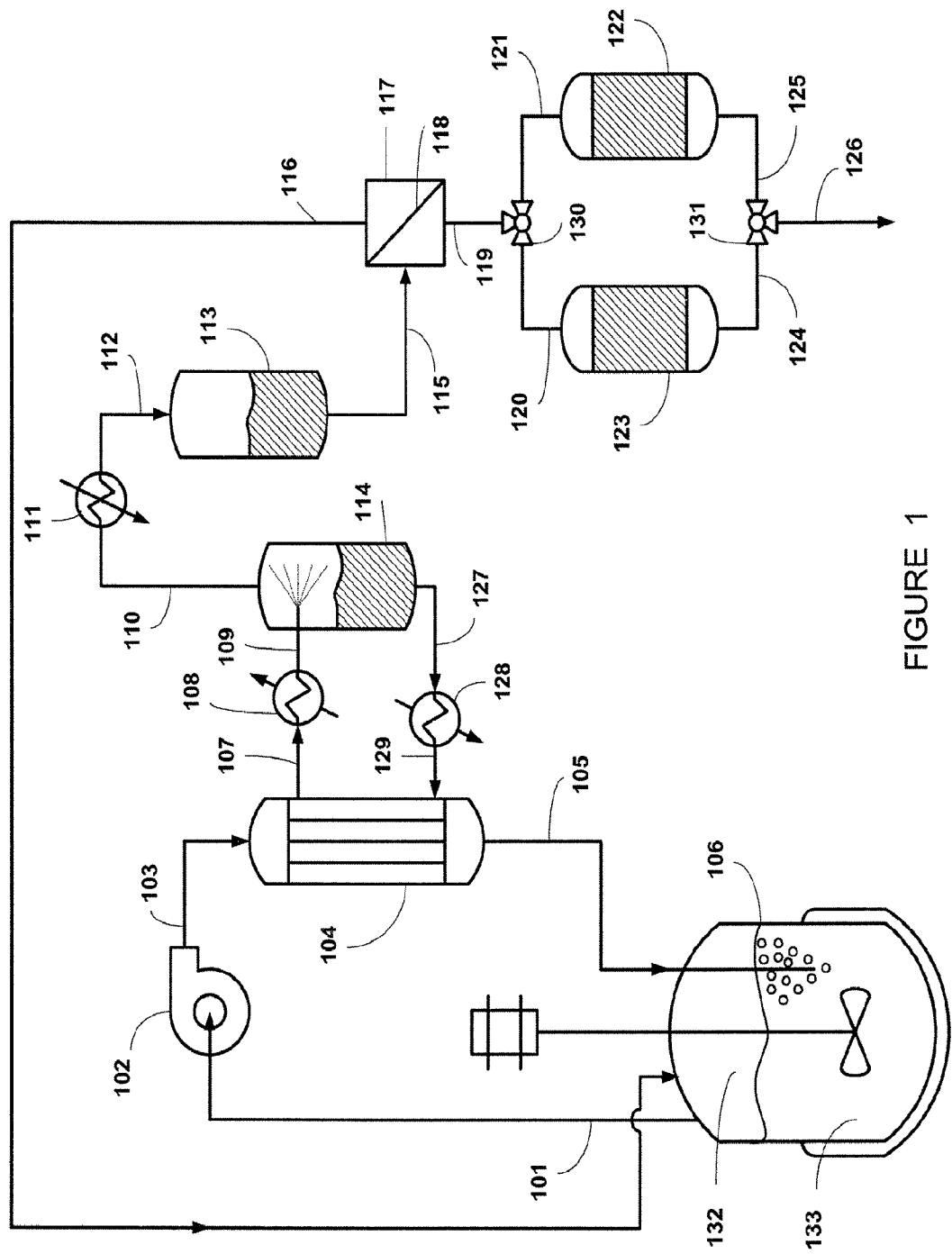
FIG. 1 shows a schematic of the process for recovering fuel grad ethanol using a membrane contactor.

In one embodiment, the ethanol extraction process disclosed herein is illustrated generally in FIG. 1. In FIG. 1, feed tank 106 contains a dilute aqueous ethanol feed which is made up of a dilute aqueous ethanol liquid phase 133 in equilibrium with a vapor phase 132. The dilute aqueous ethanol feed may contain about 20 weight percent ethanol in water, in one embodiment. In another embodiment, dilute aqueous ethanol feeds may contain about 1 weight percent to about 20 weight percent ethanol in water. One skilled in the art will recognize that ethanol produced by microbial fermentation typically generates less than about 20 weight percent ethanol due to the negative effect that the ethanol product has on the rate of fermentation. The feed may also be from about 20 weight percent ethanol to about 50 weight percent ethanol if a prior partial distillation process is put in place. Thus, the feed can come directly from a fermentation tank or from partial distillation, for example. The temperature of the dilute aqueous ethanol feed generally is in a range from about 25° C. to about 100° C.

Vapor phase 132 is withdrawn from the tank via line 101 into the suction of blower 102 which creates sufficient pressure to force the stream through line 103 and into a membrane contactor 104. Vapor in equilibrium with liquid fermentation broth (bulk solvent is water) is normally enriched in ethanol. For example, liquid containing 7.21 mole percent ethanol will be in equilibrium with vapor containing 38.91 mole percent ethanol. Therefore, a process for purifying ethanol from dilute aqueous ethanol feed begins by withdrawing the ethanol enriched vapor phase into a stream.

Figures 3A, 3B:
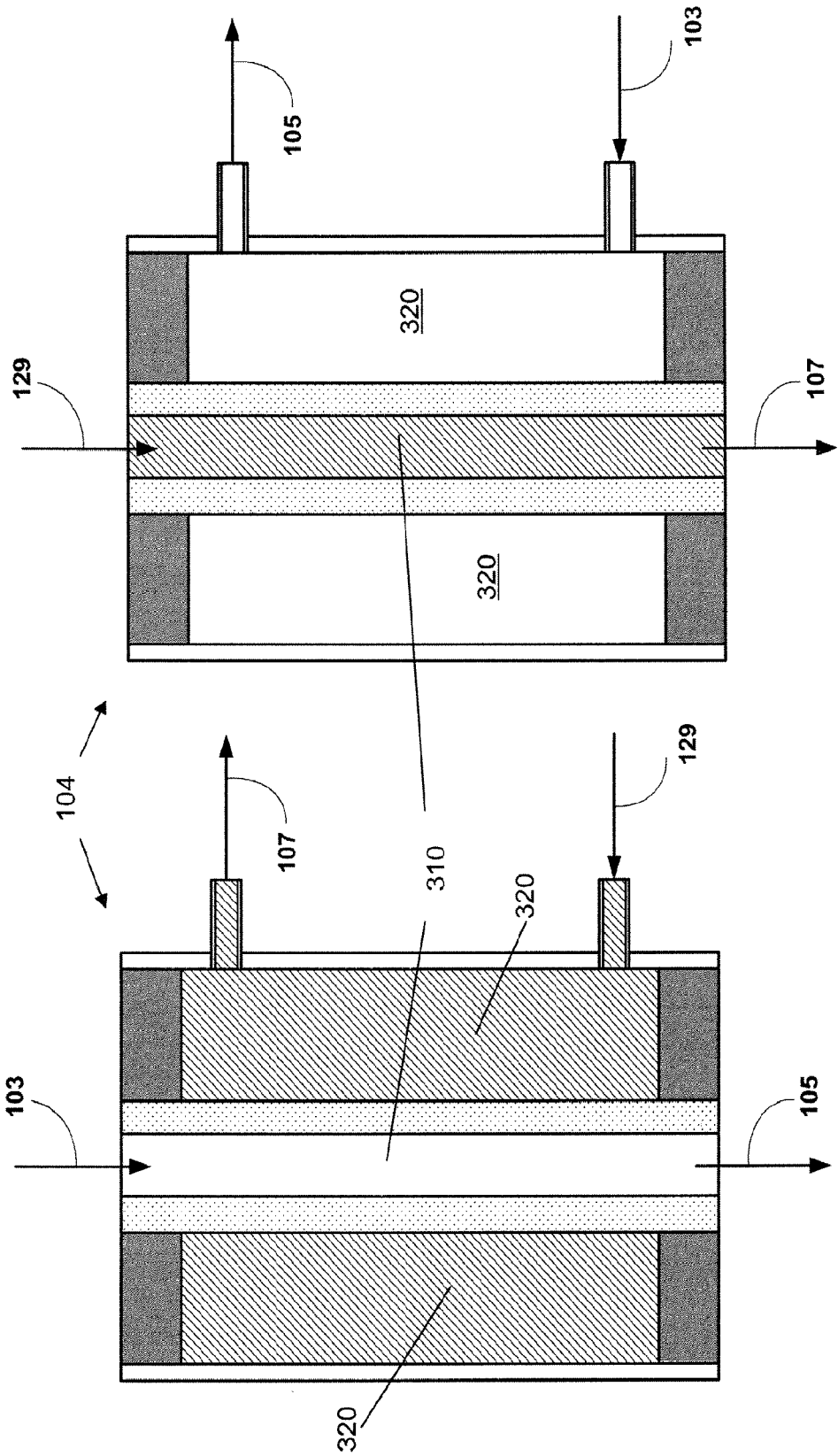
FIG. 3A shows a membrane contactor with a vapor stream circulating through an inner lumen.
FIG. 3B shows a membrane contactor with a vapor stream circulating through an outer shell.

In one embodiment, membrane contactor 104 is a hollow fiber module containing a plurality of hollow fibers potted into each end of a membrane module housing. The vapor in line 103 may be fed through lumen 310 (see FIG. 3A) of the hollow fibers and exit through line 105 which is piped below the liquid level of liquid phase 133 to create bubbles and assist in maintaining equilibrium. Concomitantly, a solvent is fed to the outer shell 320 (FIG. 3A) of membrane contactor 104 through line 129 using a pump (not shown) and circulates, for example, countercurrently to the vapor feed. Alternatively, as shown in FIG. 3B, the vapor stream of line 103 may be circulated through outer shell 320 while solvent is introduced through lumen 310. In one embodiment, the hollow fiber membranes are microporous and not wet by the solvent. Therefore, in membrane contactor 104, ethanol is transferred from vapor phase to the liquid solvent phase across a meniscus that exists in the pores of the fibers. Solvent exiting membrane contactor 104 through line 107 then contains enriched ethanol having an ethanol to water ratio ranging from about 2 to about 20, depending on the selectivity of the solvent for ethanol.

The solvent for this process may have a boiling point in excess of 200° C. in one embodiment, in excess of 250° C. in another embodiment, and in excess of 300° C., in yet another embodiment. The solvent may be chosen from unsaturated aliphatic long chain fatty acids, and esters thereof, having 16 carbons or more as exemplified by oleic acid or linoleic acid. Alternatively, the solvent may be chosen from triglycerides such as corn oil or soybean oil. In yet another embodiment, the solvent may be silicone oil. One skilled in the art will recognize that many different solvents, including but not limited to oleic acid, methyl oleate, corn oil, soybean oil, or silicone oil, may be used to extract ethanol from vapors in equilibrium with dilute aqueous ethanol mixtures and that many different membrane types and flow configurations may be used to carry out the extraction process. Stream 107 is then heated to a temperature sufficient to vaporize the extract but not the solvent in heat exchanger 108 and fed through line 109 into a flash drum 114 where the ethanol/water vapor exits through line 110 and the solvent remains in the liquid phase. Solvent exits tank 114 through line 127 and is then cooled to the desired operating temperature by heat exchanger 128 and recycled to membrane contactor 104.

Ethanol/water overhead from flash drum 114 exiting through line 110 is then condensed by heat exchanger 111, flows through line 112 and is held in tank 113 to serve as the feed to the pervaporation step. Alternatively, the vapor stream in line 110 may be fed directly to a pervaporation membrane without condensation. Thus, exchanger 111 is optional. Liquid from tank 113, which may range in temperature from about 75° C. to about 120° C. (at pressures from about 5 psig to about 75 psig) is then fed to pervaporation membrane unit 117 where feed may be contacted as a liquid with a dense (i.e. non-porous) membrane 118. Membranes for this step may include, for example, crosslinked polyvinyl alcohols. Water is selectively dissolved into membrane 118 and permeates across the membrane under a concentration gradient created by pulling a vacuum on its downstream side. Water, removed from the feed as vapor under vacuum exits the membrane unit through line 116 and is condensed to liquid form. This stream may contain some ethanol and may be recycled to the feed tank through line 116, if desired.

An enriched ethanol stream containing greater than about 95 weight percent ethanol exits the pervaporation unit 117 through line 119 and is further dried by removing a substantial portion of the remaining water using adsorption beds 122 and 123 which may contain type A zeolite molecular sieves, and which are operated in a typical swing bed fashion, where one bed is adsorbing while the other is being regenerated. Fuel-grade ethanol having less than about 0.5 weight percent water exits the molecular sieve driers though line 126 for further processing through the addition of gasoline as a denaturant.

Figure 2:
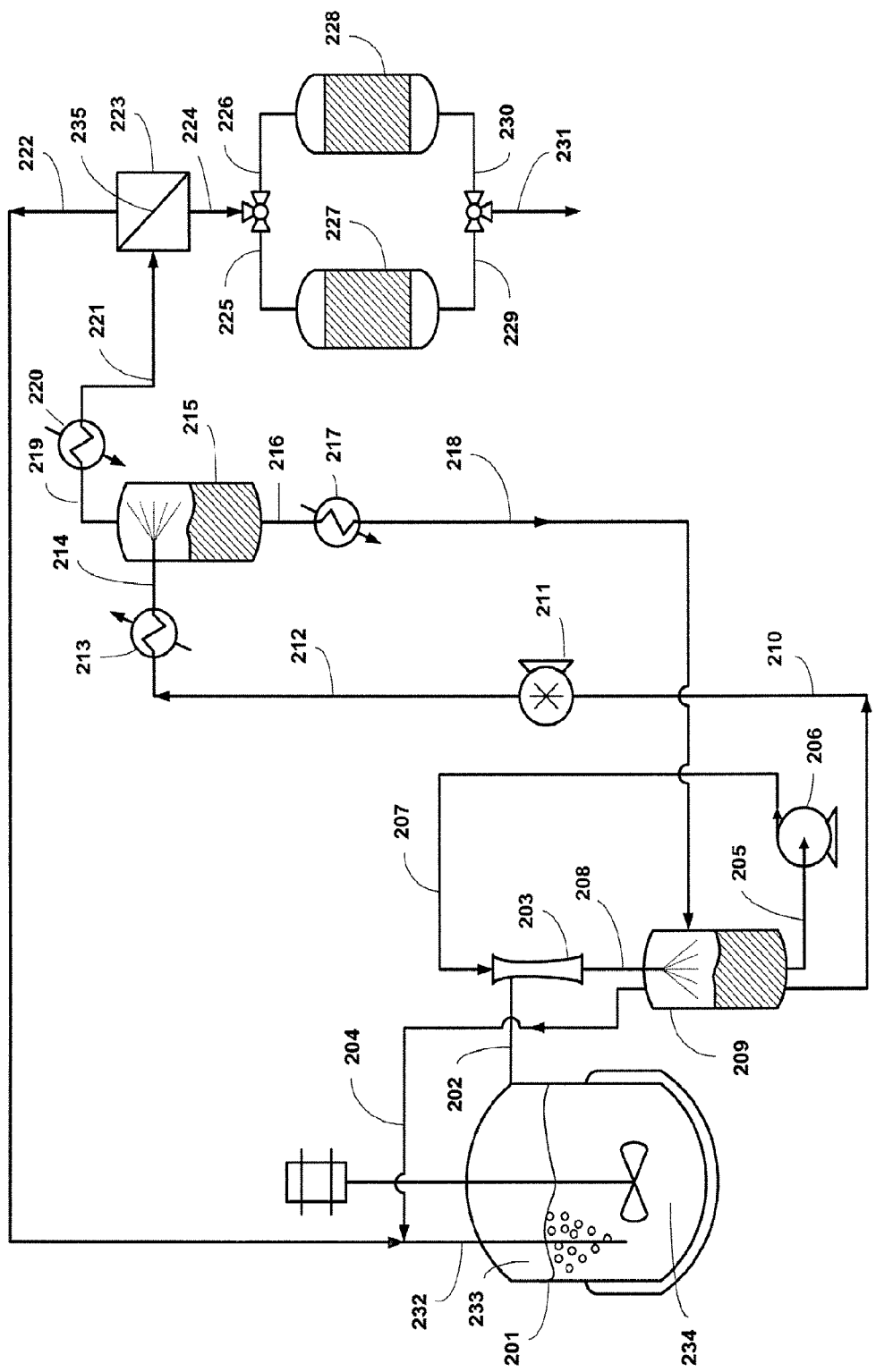
FIG. 2 shows a schematic of the process for recovering fuel grade ethanol using a Venturi nozzle.

In an alternate embodiment, in lieu of the membrane contactor a Venturi nozzle may be used as illustrated in FIG. 2. In FIG. 2, feed tank 201 contains a dilute aqueous ethanol liquid phase 234 in equilibrium with a vapor phase 233. Vapor phase 233 is withdrawn from the tank via line 202 into the suction of Venturi nozzle 203. A Venturi is a converging-diverging nozzle that works on the basis of Bernoulli's Principle to create a low pressure area at the throat (minimum diameter) of the nozzle, which low pressure area acts as a suction for vapors or liquids, thereby allowing the Venturi nozzle to replace a pump or a blower. Solvent is pumped to the Venturi nozzle through line 207 using a pump 206 and intimately mixes with the vapor feed. Solvent exiting Venturi 203 through line 208 then is collected in tank 209 and contains enriched ethanol having an ethanol to water ratio ranging from about 2:1 to about 20:1, depending on the selectivity of the solvent for ethanol. A portion of the solvent in tank 209 is drawn off through line 205 to pump 206 for delivery back to the Venturi nozzle via line 207.

A liquid slipstream 210 is withdrawn continuously from tank 209 using pump 211 and is then heated using heat exchanger 213 to a temperature sufficient to vaporize the ethanol and water but not the solvent. The heated ethanol/water/solvent mixture then exits through line 214 into flash drum 215 where the ethanol/water vapor exits overhead through line 219 and the solvent remains in the liquid phase. Solvent exits tank 215 through line 216 and is then cooled to the desired operating temperature by heat exchanger 217 and recycled to the Venturi fluid tank 209 through line 218.

Ethanol/water overhead from flash drum 215 exits through line 219 is then condensed by heat exchanger 220 (exchanger 220 is optional; and it may be desirable to send a vapor stream directly to a pervaporation membrane) and proceeds through line 221 to the pervaporation unit. This feed liquid, which may range in temperature from about 75° C. to about 120° C. (under pressure) is then fed to pervaporation membrane unit 223 where feed is contacted preferably as a liquid with a dense (i.e. non-porous) membrane 235. In one embodiment, membranes for this step may include, for example, crosslinked polyvinyl alcohols. Water is selectively dissolved into membrane 235 and permeates across the membrane under a concentration gradient created by pulling a vacuum on its downstream side. Water, removed from the feed as vapor under vacuum exits the membrane unit through line 222 and is condensed to liquid form. This stream may contain some ethanol and may be recycled to the feed tank 201, if desired.

An enriched ethanol stream containing greater than about 95 weight percent ethanol exits the pervaporation unit 223 through line 224 and is further dried using molecular sieve adsorption beds 227 and 228 which are operated in a typical swing bed fashion, where one bed is adsorbing while the other is being regenerated. Fuel-grade ethanol exits the molecular sieve driers though line 231 for further processing through the addition of gasoline as a denaturant.

Several advantages are realized through the above described purification procedures. By withdrawing the vapor phase as opposed to the liquid, no filtration is required, thereby reducing the cost of the unit and the propensity for fouling. Further, the vapor phase is enriched in ethanol relative to the liquid phase with which it in equilibrium, thereby presenting a higher ethanol content to the separation device. The use of a membrane contactor, especially a hollow fiber contactor, provides a substantial amount of area for interfacial transport without physically mixing the fluids, thereby eliminating the formation of emulsions. Membrane contactors can be used with two immiscible fluids of comparable densities (which is not possible in conventional liquid-liquid extraction) because gravity settling is not required to separate the fluids. The vacuum level attained by a Venturi nozzle can be easily adjusted by varying the flow rate of motive fluid through the nozzle; and these devices consume very little energy (only the energy to operate a pump) compared to distillation. The processes disclosed herein may therefore provide fuel-grade ethanol by more economical means than currently available.

Although the present disclosure has been described with reference to specific embodiments, these descriptions are not meant to be construed in a limiting sense. Various modifications of the disclosed embodiments, as well as alternative embodiments will become apparent to persons skilled in the art upon reference to the description. It will be understood that certain of the above-described structures, functions, and operations of the above-described embodiments are not necessary to practice such embodiments and are included in the description simply for completeness of an exemplary embodiment or embodiments. In addition, it will be understood that specific structures, functions, and operations set forth in the above and below described referenced patents and publications can be practiced in conjunction with various embodiments, but they are not essential. It is therefore to be understood that embodiments may be practiced otherwise than as specifically described without actually departing from the spirit and scope of the disclosure as defined by the appended claims. It is therefore contemplated that the claims will cover any such modifications or embodiments that fall within the true scope of the disclosure.

What is claimed is:

1. A method for recovery of fuel-grade ethanol from dilute aqueous ethanol feed in a continuous or batch-wise process, the method comprising:
    providing a feed tank having a dilute aqueous ethanol feed comprising a dilute aqueous ethanol liquid phase and a vapor phase;
    removing a portion of the vapor phase from the tank;
    circulating the portion of the vapor phase through a membrane contactor comprising an inner lumen and an outer shell;
    recovering from the membrane contactor a feed phase substantially reduced in ethanol and a solvent phase substantially enriched in ethanol;
    separating an enriched ethanol phase from the solvent phase; and
    removing a substantial amount of water from the enriched ethanol phase to produce a fuel-grade ethanol stream.

2. The method of claim 1 wherein a temperature of the dilute aqueous ethanol feed is in a range from about 25° C. to about 100° C.

3. The method of claim 1, wherein the vapor phase is circulated through the inner lumen.

4. The method of claim 1, wherein the vapor phase is circulated through the outer shell.

5. The method of claim 1 wherein the solvent phase comprises a long chain fatty acid.

6. The method of claim 1, wherein the solvent phase comprises a triglyceride.

7. The method of claim 1, wherein the solvent phase comprises silicone oil.

8. The method of claim 1 further comprising removing additional water from the enriched ethanol phase using a pervaporation membrane.

9. The method of claim 8 wherein the pervaporation membrane comprises polyvinyl alcohol.

10. The method of claim 1 further comprising removing additional water from the enriched ethanol phase by adsorption.

11. A method for recovery of fuel-grade ethanol from dilute aqueous ethanol streams, the method comprising:
    providing a feed tank having a dilute aqueous ethanol feed comprising a dilute aqueous ethanol liquid phase and a vapor phase;
    removing a portion of the vapor phase from the tank by means of a Venturi nozzle having as its working fluid a solvent with an affinity for ethanol;
    recovering from the Venturi nozzle a feed phase substantially reduced in ethanol and a solvent phase substantially enriched in ethanol;
    separating an enriched ethanol phase from the solvent phase;
    removing water from the enriched ethanol phase using a pervaporation membrane to produce a further enriched ethanol stream and an aqueous stream substantially depleted in ethanol; and
    removing a substantial amount water from the enriched ethanol stream recovered from to produce a fuel-grade ethanol stream.

12. The method of claim 11, wherein the temperature of the dilute aqueous ethanol feed is in a range from about 25° C. to about 100° C.

13. The method of claim 11, wherein the working fluid comprises a long chain fatty acid.

14. The method of claim 11, wherein the working fluid comprises a triglyceride.

15. The method of claim 11, wherein the working fluid comprises a silicone oil.

16. The method of claim 11, wherein the pervaporation membrane comprises polyvinyl alcohol.

17. The method of claim 11, wherein water is removed by adsorption.

* * * * *